US00PP26163P3

(12) United States Plant Patent
Suzuki

(10) Patent No.: US PP26,163 P3
(45) Date of Patent: Nov. 24, 2015

(54) ***PRIMULA* PLANT NAMED 'HAK-P-01'**

(50) Latin Name: ***Primula filchnera*×*Primula sinensis***
Varietal Denomination: HAK-P-01

(71) Applicant: Yoshikuni Suzuki, Nagakute (JP)

(72) Inventor: Yoshikuni Suzuki, Nagakute (JP)

(73) Assignee: J & H JAPAN INC., Aichi (JP)

( * ) Notice: Subject to any disclaimer, the term of this patent is extended or adjusted under 35 U.S.C. 154(b) by 122 days.

(21) Appl. No.: 13/999,211

(22) Filed: Jan. 30, 2014

(65) Prior Publication Data

US 2015/0216097 P1 Jul. 30, 2015

(51) Int. Cl.
*A01H 5/00* (2006.01)

(52) U.S. Cl.
USPC ..... Plt./472

(58) Field of Classification Search
USPC ..... Plt./472
See application file for complete search history.

*Primary Examiner* — Annette Para

(57) ABSTRACT

A new cultivar of *Primula* plant named 'HAK-P-01' that is characterized by a short overall height, a compact habit and flowers that have a red-purple upper side and a red-purple under side with a white base.

1 Drawing Sheet

Botanical classification: *Primula filchnera*×*Primula sinensis*.

Variety denomination: 'HAK-P-01'.

BACKGROUND OF THE INVENTION

The present invention relates to a new and distinct cultivar of *Primula* plant botanically known as *Primula filchnera*× *Primula sinensis* and hereinafter referred to by the cultivar name 'HAK-P-01'.

'HAK-P-01' originated from the self-crossing of the female or seed parent *Primula filchnera*×*Primula sinensis* 'Thirtyone' (U.S. Plant Pat. No. 20,220) and the male or pollen parent *Primula filchnera*×*Primula sinensis* 'Thirtyone'. The crossing was conducted in February of 2007 in Aichi, Japan. The resulting seeds were subsequently planted and grown. The cultivar 'HAK-P-01' was selected by the inventor in February of 2008 in a controlled environment as a single plant within the progeny of the stated cross in a cultivated area of Aichi, Japan.

Asexual reproduction of the new cultivar 'HAK-P-01' first occurred by tissue culture in February of 2008 in Aichi, Japan. Since that time, under careful observation, the unique characteristics of the new cultivar have been uniform, stable and reproduced true to type in successive generations of asexual reproduction.

SUMMARY OF THE INVENTION

The following represent the distinguishing characteristics of the new *Primula* cultivar 'HAK-P-01'. These traits in combination distinguish 'HAK-P-01' as a new and distinct cultivar apart from other existing known varieties of *Primula*.

1. *Primula* 'HAK-P-01' exhibits a short overall height.
2. *Primula* 'HAK-P-01' exhibits a compact habit.
3. *Primula* 'HAK-P-01' exhibits flowers having a red-purple upper side and a red-purple under side with a white base.

The closest comparison cultivar is the co-pending application *Primula* 'HAK-P-02'. 'HAK-P-01' is distinguishable from 'HAK-P-02' by the following characteristics:

1. *Primula* 'HAK-P-01' exhibits flowers having petals with a red-purple upper side and a red-purple under side with a white base. In comparison, the petals of 'HAK-P-02' have a purple upper side with a yellow-green base and a purple under side with a white base.

'HAK-P-01' is distinguishable from the female parent and the male parent 'Thirtyone' by the following characteristics:

1. *Primula* 'HAK-P-01' exhibits a shorter overall height than the overall height of 'Thirtyone'.
2. *Primula* 'HAK-P-01' exhibits a more compact habit than 'Thirtyone'.
3. *Primula* 'HAK-P-01' exhibits flowers having petals with a red-purple upper side and a red-purple under side with a white base. In comparison, the petals of 'Thirtyone' have a purple-violet upper side and a purple-violet under side with a white base.

BRIEF DESCRIPTION OF THE DRAWING

The accompanying photograph illustrates the distinguishing traits of *Primula* 'HAK-P-01'. The plant in the photograph shows an overall view of a 6 month old plant. The photograph was taken using conventional techniques and although colors may appear different from actual colors due to light reflectance it is as accurate as possible by conventional photographic techniques.

BOTANICAL DESCRIPTION OF THE PLANT

The following is a detailed description of the new *Primula* cultivar named 'HAK-P-01'. Data was collected in Aichi, Japan from 6 month plants grown in a glass greenhouse in 15 cm. diameter containers. The time of year was Winter and the temperature range was 10-35 degrees Centigrade during the day and 10-20 degrees Centigrade at night. The light level was 50 klux. No photoperiodic treatments or growth retards were used. Color determinations are in accordance with The Royal Horticultural Society Colour Chart 2007 edition, except where general color terms of ordinary dictionary significance are used. The growing requirements are similar to the species. 'HAK-P-01' has not been tested under all possible conditions and phenotypic differences may be observed with variations in environmental, climatic, and cultural conditions, however, without any variance in genotype.

Botanical classification: *Primula filchnera*×*Primula sinensis* 'HAK-P-01'.

Annual or perennial: Perennial.

Parentage: 'HAK-P-01' is the product of the self-crossing of *Primula filchnera*×*Primula sinensis* 'Thirtyone'.

Plant type: Pot plant.

Plant shape: Upright.

Suitable container size: 15 cm. pots.

Plant height: 25 cm. in height.

Plant width: 30 cm. in width.

Vigor: Moderate.

Low temperature tolerance: −5° Centigrade.

High temperature tolerance: 40° Centigrade.

Propagation: Tissue culture.

Time to initiate roots: Three to four weeks at 18° C. to 25° C.

Time to produce a rooted cutting: Five to six weeks at 18° C. to 25° C.

Crop time: Approximately 6 months.

Root system: Fine and fibrous.

Stem:

*Basal branching.*—Yes.

*Average number of lateral branches.*—10.

*Pinching required.*—No.

Foliage:

*Leaf arrangement.*—Basal.

*Compound or single.*—Single.

*Leaf shape.*—Cordate.

*Leaf apex.*—Obtuse.

*Leaf base.*—Acute.

*Leaf length.*—23 cm. in length.

*Leaf width.*—12 cm. in width.

*Texture.*—Rugose both surfaces.

*Pubescence.*—Both sides covered with short hairs.

*Leaf margin.*—Crenate.

*Venation pattern.*—Pinnate.

*Young leaf color* (*upper surface*).—139A.

*Young leaf color* (*lower surface*).—139B, 187B toward base.

*Mature leaf color* (*upper surface*).—139A.

*Mature leaf color* (*lower surface*).—139B, 187B toward base.

*Vein color* (*upper surface*).—N187C.

*Vein color* (*under surface*).—139B, 187B toward base.

*Leaf attachment.*—Petiolate.

*Petiole dimensions.*—8 cm. in length, and 7.0 mm. in diameter.

*Petiole color.*—187A.

*Petiole pubescence.*—Covered with short hairs.

Flower:

*Flower type.*—Single rounded and salverform flowers arranged on umbels on upright and strong peduncles; flowers face mostly upright. Freely flowering habit with 5 to 10 flowers and buds per umbel.

*Inflorescence dimensions.*—10 cm. in length and 10 cm. in width.

*Quantity of flowers and buds per plant.*—20.

*Natural flowering season.*—April to July.

*Time to flower.*—6 months.

*Rate of flower opening.*—50 percent of flowers are open at one time.

*Fragrance.*—Strong, irritating.

*Flower bud length.*—1.5 cm.

*Flower bud diameter.*—5 mm.

*Flower bud shape.*—Elliptic.

*Bud color.*—146A, towards base N79B.

*Flower shape.*—Salverform.

*Flower dimensions.*—3.5 cm. in diameter and 1.5 cm. in height.

*Flower longevity.*—7 to 14 days.

*Number of petals.*—6.

*Fused or unfused.*—Fused.

*Petal shape.*—Obcordate.

*Petal margin.*—Crenate.

*Petal apex.*—Shallow emarginate.

*Petal base.*—Fused.

*Petal texture.*—Glabrous both surfaces.

*Petal length.*—1.5 cm.

*Petal width.*—1.25 cm.

*Petal color when opening* (*upper side*).—61B.

*Petal color when opening* (*under side*).—61B with base N155A.

*Petal color fully opened* (*upper side*).—60A.

*Petal color fully opened* (*under side*).—60A with base N155A.

*Petal color fading to.*—Not fading.

*Self-cleaning or persistent*—Self-cleaning.

Sepals:

*Number of sepals.*—5 fused.

*Sepal shape.*—Lanceolate.

*Sepal margin.*—Serrate.

*Sepal apex.*—Acute.

*Sepal texture inner side.*—Glabrous.

*Sepal texture outer side.*—Pubescent.

*Sepal dimensions.*—2 mm. in length and 2 mm. in width.

*Mature sepal color* (*inner side*).—144A with base N77D.

*Mature sepal color* (*under side*).—144A with base N77D.

Peduncle:

*Peduncle dimensions.*—10 cm. in length and 6 mm. in diameter.

*Peduncle angle.*—0 degrees.

*Peduncle strength.*—Strong.

*Peduncle texture.*—Rough, pubescent.

*Peduncle color.*—187A.

Pedicels:

*Pedicel dimensions.*—3.5 cm. in length and 1.5 mm. in diameter.

*Pedicel strength.*—Moderate.

*Pedicel color.*—187A.

Reproduction organs:

*Stamen number.*—4.

*Anther shape.*—Oblong.

*Anther length.*—0.5 mm.

*Anther color.*—2C.

*Amount of pollen.*—None.

Fruit and seed: None, sterile.

Disease and pest resistance: Disease and pest resistance has not been observed.

The invention claimed is:

1. A new and distinct variety of *Primula* plant named 'HAK-P-01' as described and illustrated.

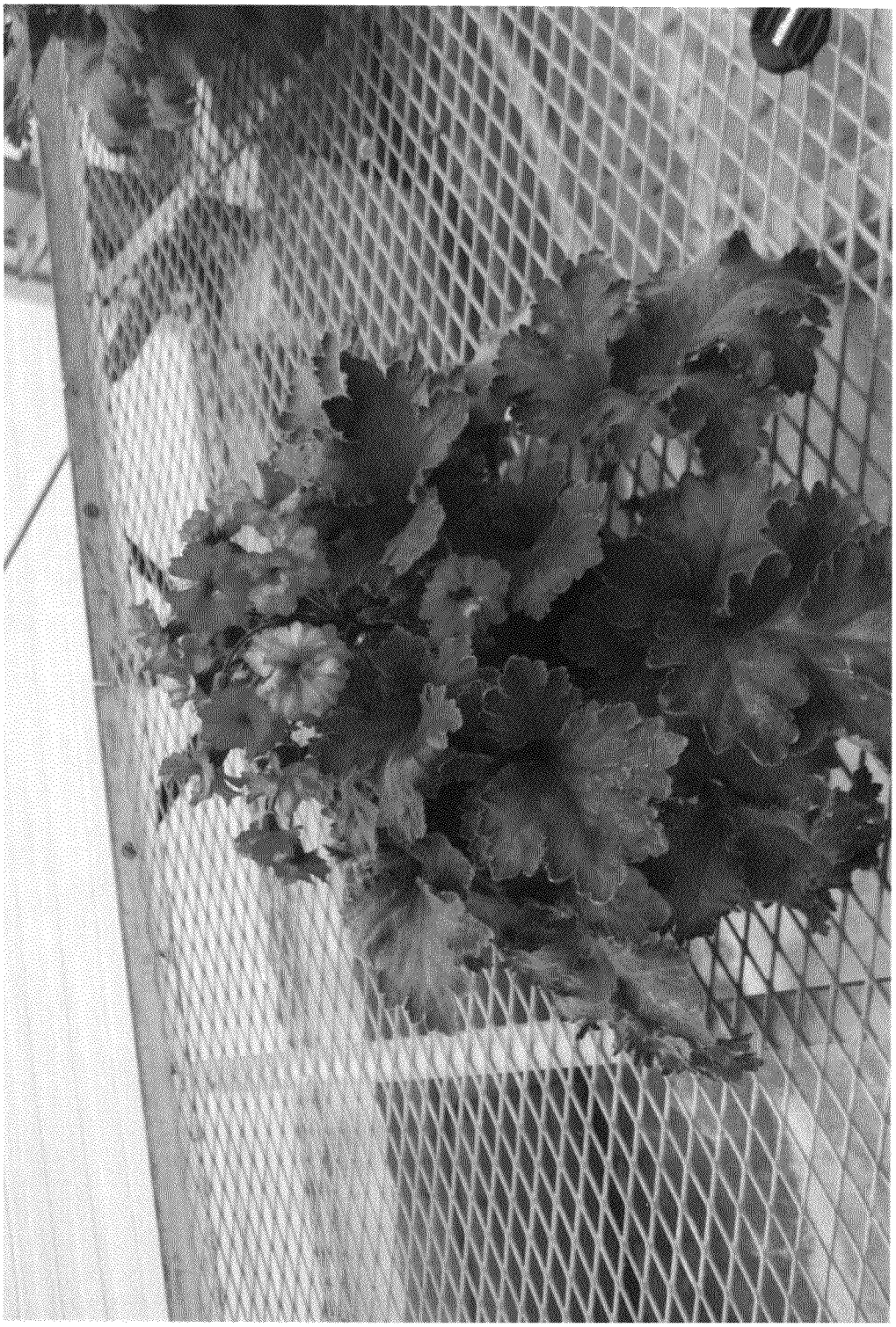

* * * * *